US006761453B2

(12) United States Patent
Wilson

(10) Patent No.: US 6,761,453 B2
(45) Date of Patent: *Jul. 13, 2004

(54) SYSTEMS AND METHODS FOR PERFORMING AN EYE EXAMINATION

(76) Inventor: Ralph C. Wilson, 25 Orchard Dr., Queensbury, NY (US) 12804

( * ) Notice: Subject to any disclaimer, the term of this patent is extended or adjusted under 35 U.S.C. 154(b) by 202 days.

This patent is subject to a terminal disclaimer.

(21) Appl. No.: 09/976,208

(22) Filed: Oct. 11, 2001

(65) Prior Publication Data

US 2002/0021411 A1 Feb. 21, 2002

Related U.S. Application Data

(63) Continuation-in-part of application No. 09/583,189, filed on May 30, 2000.

(51) Int. Cl.$^7$ ................................................. A61B 3/10
(52) U.S. Cl. ...................................................... 351/205
(58) Field of Search ................................. 351/221, 222, 351/223, 233, 237, 239, 243; 600/558; 128/920

(56) References Cited

U.S. PATENT DOCUMENTS

| | | | |
|---|---|---|---|
| 1,284,103 A | | 11/1918 | Herrick |
| 1,601,653 A | | 9/1926 | Stanley |
| 3,969,020 A | * | 7/1976 | Lynn et al. ................. 351/237 |
| 4,611,893 A | | 9/1986 | Schrier |
| 4,998,820 A | | 3/1991 | Salibello et al. |
| 5,206,671 A | | 4/1993 | Eydelman et al. |
| 5,347,330 A | | 9/1994 | Hofeldt |
| 5,436,681 A | | 7/1995 | Michaels |
| 5,589,897 A | | 12/1996 | Sinclair et al. |
| 5,617,157 A | * | 4/1997 | Shalon et al. ................ 351/222 |
| 5,694,199 A | | 12/1997 | Rodriguez |
| 5,877,841 A | | 3/1999 | Jeon |
| 5,880,814 A | | 3/1999 | McKnight et al. |
| 5,946,075 A | | 8/1999 | Horn |
| 6,027,217 A | | 2/2000 | McClure et al. |
| 6,033,076 A | | 3/2000 | Braeuning et al. |

OTHER PUBLICATIONS

OPTX 20/20, Reading Lenses for Sunglasses, http:\\www.neoptx.com\eyetest\eyetest.html, Mar. 16, 2000.

* cited by examiner

*Primary Examiner*—George Manuel
(74) *Attorney, Agent, or Firm*—Ronald A. D'Alessandro; Hoffman, Warnick & D'Alessandro LLC

(57) ABSTRACT

Systems and methods for performing an eye examination are disclosed. In particular, an object is recorded by a recording mechanism. The recording is transferred to a computer system, which is accessible to users. As users view the recording of the object, the appearance thereof is altered. The user will observe the various appearances and select the appearance that is the best or most clear. A prescription will be assigned to each appearance so that upon selection by a user, the prescription can be noted and used to obtain any necessary eye wear. The present invention is useful in detecting and diagnosing various ocular disorders or refractive errors such as emmetropia, myopia, hyperopia, astigmatism, presbyopia and the need for prismatic lenses.

6 Claims, 12 Drawing Sheets

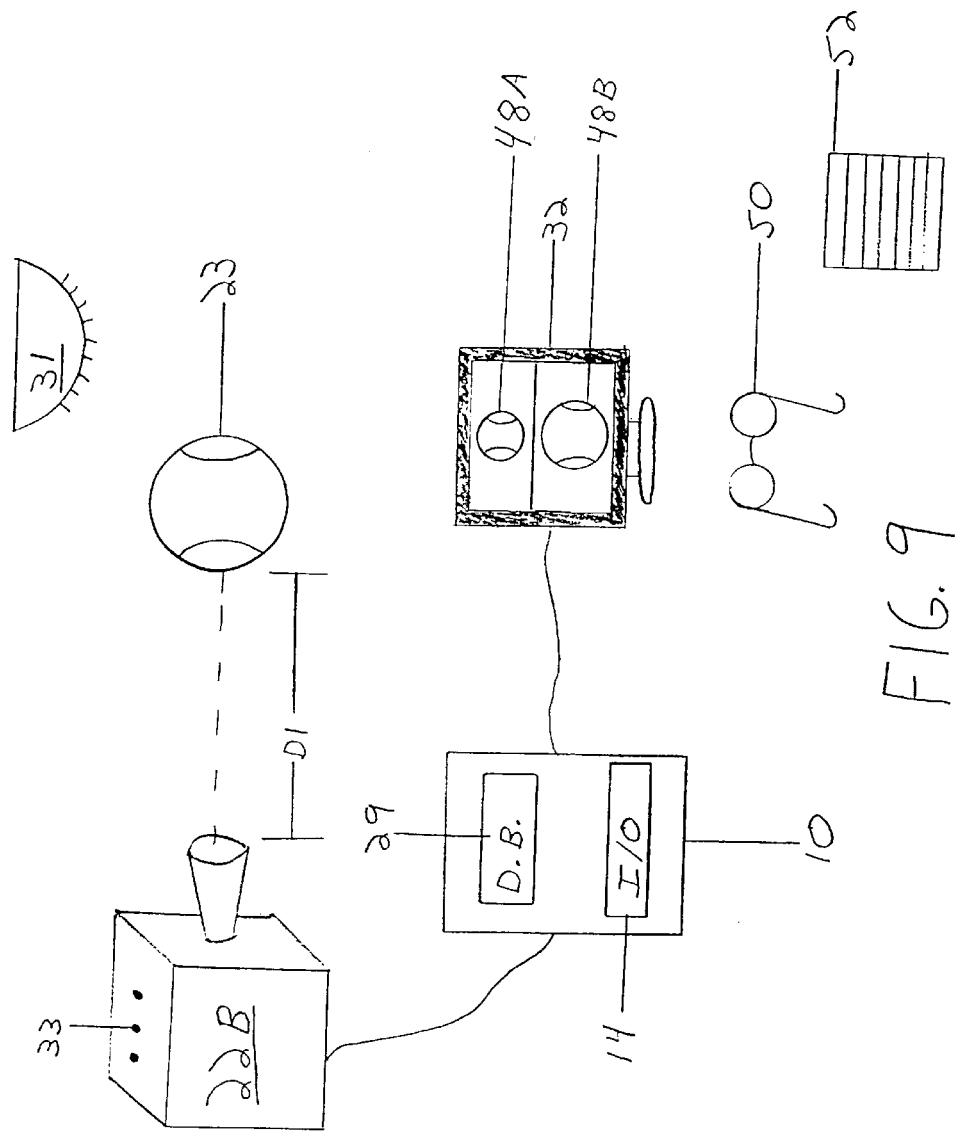

SYSTEMS AND METHODS FOR PERFORMING AN EYE EXAMINATION

This application is a continuation-in-part application of U.S. Ser. No. 09/583,189, filed May 30, 2000, and currently pending

BACKGROUND OF THE INVENTION

1. Technical Field

The present invention generally relates to systems and methods for performing an eye examination. More particularly the present invention generally relates to self-administered, computerized systems and methods for diagnosing an ocular disorder, such as a refractive error, and/or determining an eye wear prescription by altering the appearance of a recorded object.

2. Background Art

As technology increases and the popularity of the Internet continues to grow, the ability to perform everyday functions on-line becomes more prevalent. For example, users can now perform a variety of activities ranging from purchasing merchandise to securing travel reservations through world wide web sites. With the increasing capabilities of the Internet, users are now beginning to seek professional services, such as legal and medical services, while on-line.

Heretofore, many have attempted to provide on-line medical tests. Examples of this are shown in the following references.

World Wide Website neoptx.com/eyetest/eyetest.html;

U.S. Pat. No. 6,033,076 Braeuning et al.; and

U.S. Pat. No. 6,027,217 McClure et al.

World Wide Website neoptx.com/eyetest/eyetest.html teaches an on-line reading test. In particular, this reference displays a body of text to a user at different magnification levels. The user is asked to select the level that presents the body of text most clearly. This reference, however, fails to provide any optics or follow any examination protocol beyond a self-administered reading test. In contrast, the test relies on bodies of text in JPEG format that are merely "blown-up" or increased in font size relative to one another. Such manipulation fails to provide any accurate basis for a user to determine their most appropriate reading eye wear prescription. In addition, a reading prescription is the only "measurement" that can be made.

U.S. Pat. Nos. 6,033,076 to Braeuning et al. and 6,027,217 to McClure et al., hereby incorporated by reference, disclose the on-line testing of patients for various ocular disorders. In particular, the systems present visual stimuli to a patient whose responses are transmitted to an interpretation system. The interpretation system compares the patient's responses to "normal" reactions in order to make a diagnosis. Problems with these systems include the need to provide stimuli and sensing equipment to the patient. In addition, the comparison of the patient responses to normal reactions requires constant updating of the interpretation systems.

In view of the forgoing, there is a long felt need for an on-line system and method that allows a website user/patient to be accurately tested and diagnosed for various ocular disorders such as refractive error. There is also a need for such a system and method to not require a user to obtain extensive testing and sensing equipment to perform the test. In addition, there is a further need for the system and method to make a diagnosis/prescription without requiring the comparison of the user's response to those exhibited by "normal" patients to make a diagnosis/prescription.

SUMMARY OF THE INVENTION

The present invention overcomes the problems associated with existing systems by providing computerized systems and methods for performing eye examinations. In particular, the present invention allows, inter alia, a user to access a recording of an object via a computer system. Once accessed, the user will view the recording (i.e., the appearance of the object) as it is displayed on a display system. The appearance of the object is then altered so that the user can select the best or most clear appearance. A conversion system assigns a prescription to each appearance so that upon selection of a particular appearance, a user can identify an ocular disorder (e.g., refractive error) and/or obtain the corresponding prescription.

According to a first aspect of the present invention, a system for performing an eye examination is provided. The system comprises: (1) a computer system linked to an auto-refractor; (2) a display linked to the computer system for displaying an image from the auto-refractor; and (3) a recording mechanism for recording a response of a user's eye to the displayed image, wherein a prescription is determined from the recorded response.

According to a second aspect of the present invention, a system for performing an eye examination is provided. The system comprises: (1) an image generated by an auto-refractor; (2) a computer system linked to the auto-refractor for receiving the generated image; (3) a display linked to the computer system for displaying the received image; and (4) a recording mechanism for recording a response of a user's eye to the displayed image, wherein a prescription is determined from the recorded response by the auto-refractor.

According to a third aspect of the present invention, a system for performing an eye examination is provided. The system comprises: (1) a computer system having access to an image of an object as recorded by a recorded mechanism, wherein a focus of the object is altered over time by manipulating the recording mechanism; (2) a display for displaying the image, wherein the display includes a selection system for allowing a user to select a focus level; and (3) a converting system, executable by the computer system, for converting the selected focus level into a prescription.

According to a fourth aspect of the present invention, a system for performing an eye examination is provided. The system comprises: (1) a computer system having access to an image of an object as recorded by a recording mechanism, wherein a magnification of the object is altered over time by manipulating the recording mechanism; (2) a display for displaying the image, wherein the display includes a selection system for allowing a user to select a particular magnification level; and (3) an image selection system, executable by the computer system, for displaying subsequent images of the object at the selected magnification level.

It is therefore an advantage of the present invention to provide computerized systems and methods for a patient-administered eye examination. It is a further advantage of the present invention to provide such systems and methods so that a user can be tested and diagnosed for refractive errors without having to first obtain extensive stimuli and sensing equipment. It is a further advantage of the present invention to provide systems and methods for performing eye examinations that do not require comparison of a particular user's responses to responses of other users. It should be understood that although the present invention is useful in diagnosing and prescribing treatment for refractive errors, other ocular disorders (e.g., color blindness) can be diagnosed and prescribed for as well.

The preferred embodiment of the present invention is designed to solve the problems herein described and other problems not discussed, which are discoverable by a skilled artisan.

BRIEF DESCRIPTIONS OF THE DRAWINGS

These and other features and advantages of this invention will be more readily understood from the following detailed description of the various aspects of the invention taken in conjunction with the accompanying drawings in which:

FIG. 9 depicts a system for performing an eye examination in accordance with a fourth embodiment of the present invention.

Figure 1:
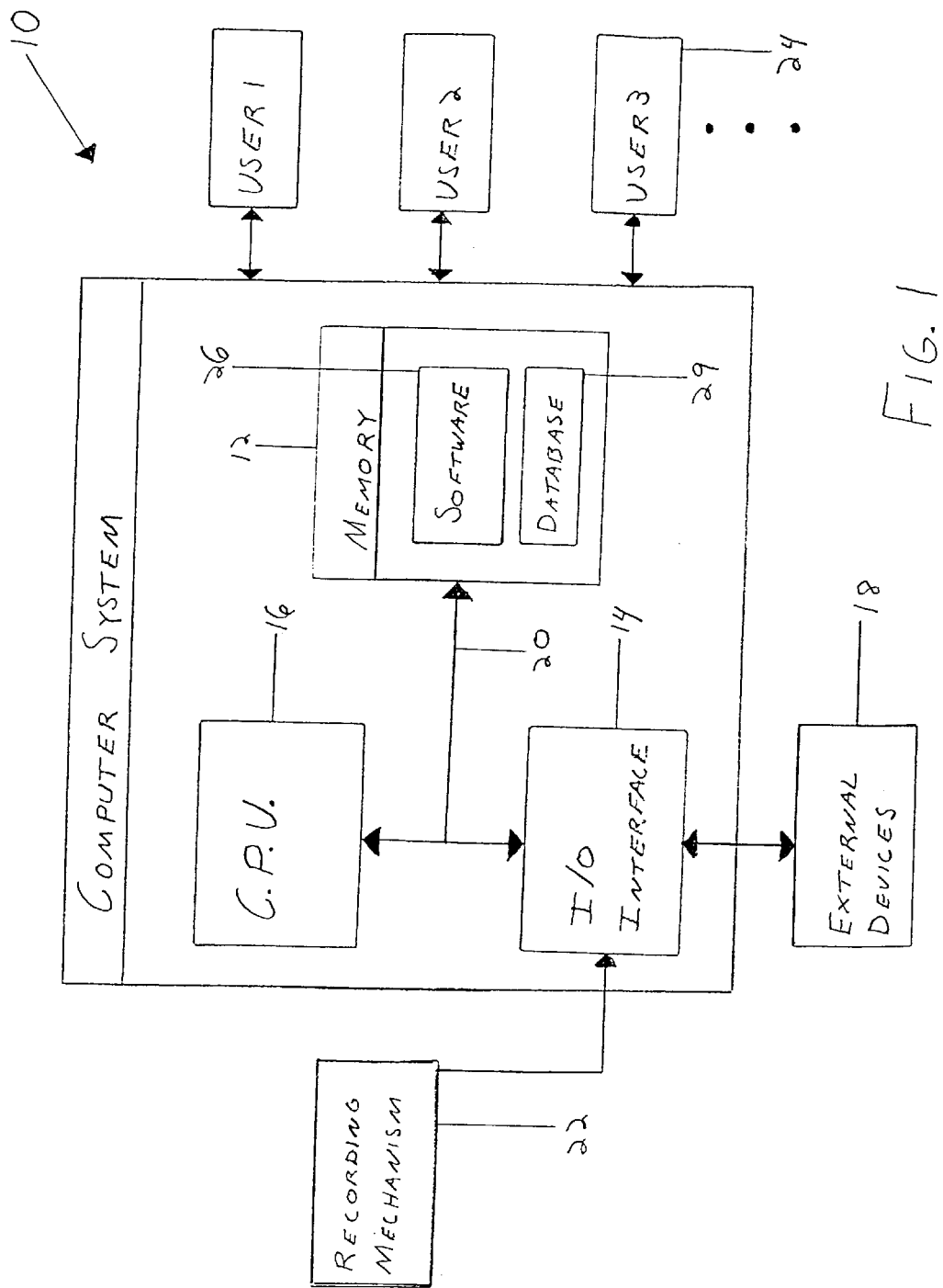
FIG. 1 depicts a block diagram of a computer system having an examination system in accordance with the present invention.

It is noted that the drawings of the invention are not to scale. The drawings are merely schematic representations, not intended to portray specific parameters of the invention. The drawings are intended to depict only typical embodiments of the invention, and therefore should not be considered as limiting the scope of the invention. In the drawings, like numbering represents like elements between the drawings.

DETAILED DESCRIPTION OF THE DRAWINGS

Referring now to FIG. 1, a computer system 10 depicting the examination system of the present invention is shown. The computer system generally comprises memory 12, input/output interfaces 14, a central processing unit (CPU) 16, external devices/resources 18, and bus 20. Memory 12 may comprise any known type of data storage and/or transmission media, including magnetic media, optical media, random access memory (RAM), read-only memory (ROM), a data cache, a data object, etc. Moreover, memory 12 may reside at a single physical location, comprising one or more types of data storage, or be distributed across a plurality of physical systems in various forms. CPU 16 may likewise comprise a single processing unit, or be distributed across one or more processing units in one or more locations, e.g., on a client and server.

I/O interfaces 14 may comprise any system for exchanging information from an external source. External devices 18 may comprise any known type of external device, including a CRT, LED screen, hand held device, keyboard, mouse, voice recognition system, speech output system, printer, facsimile, pager, etc. Bus 20 provides a communication link between each of the components in the computer system 10 and likewise may comprise any known type of transmission link, including electrical, optical, wireless, etc. In addition, although not shown, additional components, such as cache memory, communication systems, system software, etc., may be incorporated into computer system 10.

Stored in memory 12 is database 29 and software 26 for storing and processing the appearance of a viewable object. The viewable object may be captured/recorded by a recording mechanism 22 or may comprise a computer-generated object. In addition, if a real-time system is preferred, the database 29 can be eliminated and the recording or generation of the object can be fed directly to the computer system 10 through to an end user. "Real-time" for the purposes of the present invention means that the object is captured/recorded by the recording mechanism or generated as a patient is being tested. The recording is fed directly to the computer system 10 for the immediate examination of a patient without being held in the database 29.

As used herein, a best appearance of the object is determined by the particular patient being tested. Accordingly, the best appearance may be one having, inter alia, the clearest focus. However, it should be understood that the criteria for determining a best appearance may change depending on the particular ocular disorder or refractive error being tested. For example, in a test for color blindness, the best appearance may be determined on the basis of color.

Software 26 will be described in more detail below but generally comprises a system for displaying and altering an appearance of the object and for converting the appearance into an eye prescription. Thus, as the appearance of the object is altered, the eye prescription will be altered as well. In addition, under an alternative embodiment of the present invention, software 26 also includes an image processing system that allows a user to manually control the appearance of the object. It should be understood that in giving a prescription for correcting a refractive error/ocular disorder, a diagnosis is also being made. Accordingly, although the term prescription is used repeatedly herein, the present invention can also report a diagnosis.

A user 24 will access the computer system 10 to self-administer an eye examination via a direct terminal connected to the computer system 10, or via a remote workstation in a client server environment. In the case of the latter, the client and server may be connected via the Internet, wide area networks (WAN), local area networks (LAN) or other private networks. The server and client may utilize conventional token ring connectivity for WAN, LAN, or other private networks, or Ethernet, or other conventional communications standards. Where the client is connected to the system server via the Internet, connectivity could be provided by conventional TCP/IP sockets-based protocol. In this instance, the client would utilize an Internet service provider outside the system to establish connectivity to the system server within the system.

The user 24 accesses the computer system 10 to gain access to the recording of the object. While viewing the appearance of the object as it is altered, the user 24 will select the appearance that best meets the user's viewing preference (e.g., the most clear or focused appearance). Once selected, the user will note the corresponding prescription for the selected appearance. It should be understood that the present invention is useful in diagnosing and/or determining eye prescriptions for a variety of refractive errors. For example, the present invention is useful in diagnosing, inter alia, emmetropia, myopia, hyperopia, astigmatism, presbyopia and prismatic correction.

It is understood that the present invention can be realized in hardware, software, or a combination of hardware and software. As indicated above, the computer system 10 according to the present invention can be realized in a centralized fashion in a single computerized workstation, or in a distributed fashion where different elements are spread across several interconnected computer systems (e.g., a network). Any kind of computer system—or other apparatus adapted for carrying out the methods described herein—is suited. A typical combination of hardware and software could be a general purpose computer system with a computer program that, when loaded and executed, controls the computer system 10 such that it carries out the methods described herein. Alternatively, a specific use computer, containing specialized hardware for carrying out one or more of the functional tasks of the invention could be utilized. The present invention can also be embedded in a computer program product, which comprises all the features enabling the implementation of the methods described herein, and which-when loaded in a computer system—is able to carry out these methods. Computer program, software program, program, or software, in the present context mean any expression, in any language, code or notation, of a set of instructions intended to cause a system having an information processing capability to perform a particular function either directly or after either or both of the following: (a) conversion to another language, code or notation; and/or (b) reproduction in a different material form.

Figure 2:
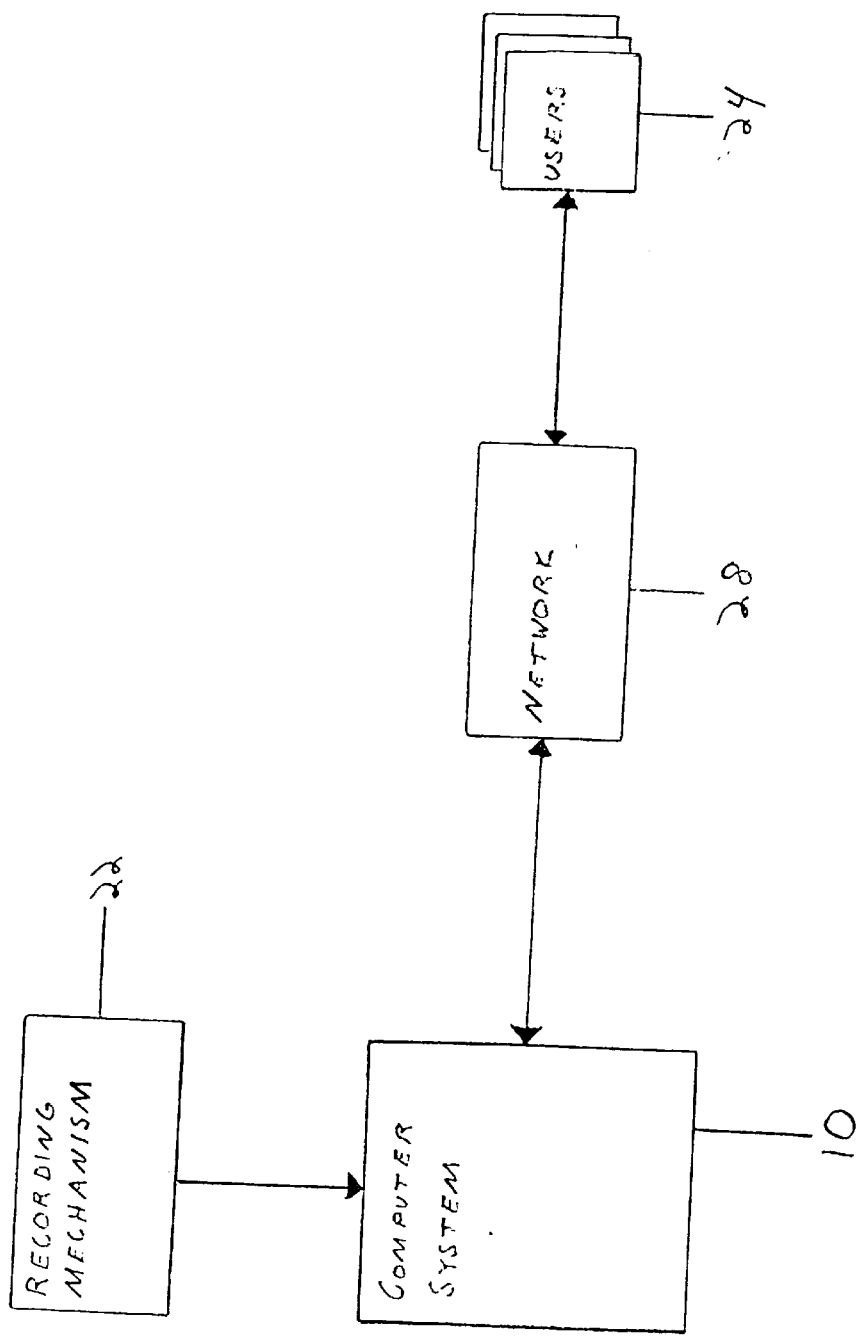
FIG. 2 depicts a block diagram of a system for performing an eye examination over a network in accordance with the present invention.

Referring now to FIG. 2, the system for performing an eye examination is shown implemented via a network 28 such as any of those described above (e.g., Internet, WAN, LAN, etc.). In particular, the recording mechanism will record/capture an object. The computer system 10 will have access to the recording either through a direct linking, remote linking, transfer of a recordable medium containing the recording, or any other way known to those of ordinary skill in the art. Users 24 can then access the computer system 10 via network 28 and view the recording. The users 24 will view the appearance of the object as it is altered and select the appearance most clear to him/her.

Figure 3:
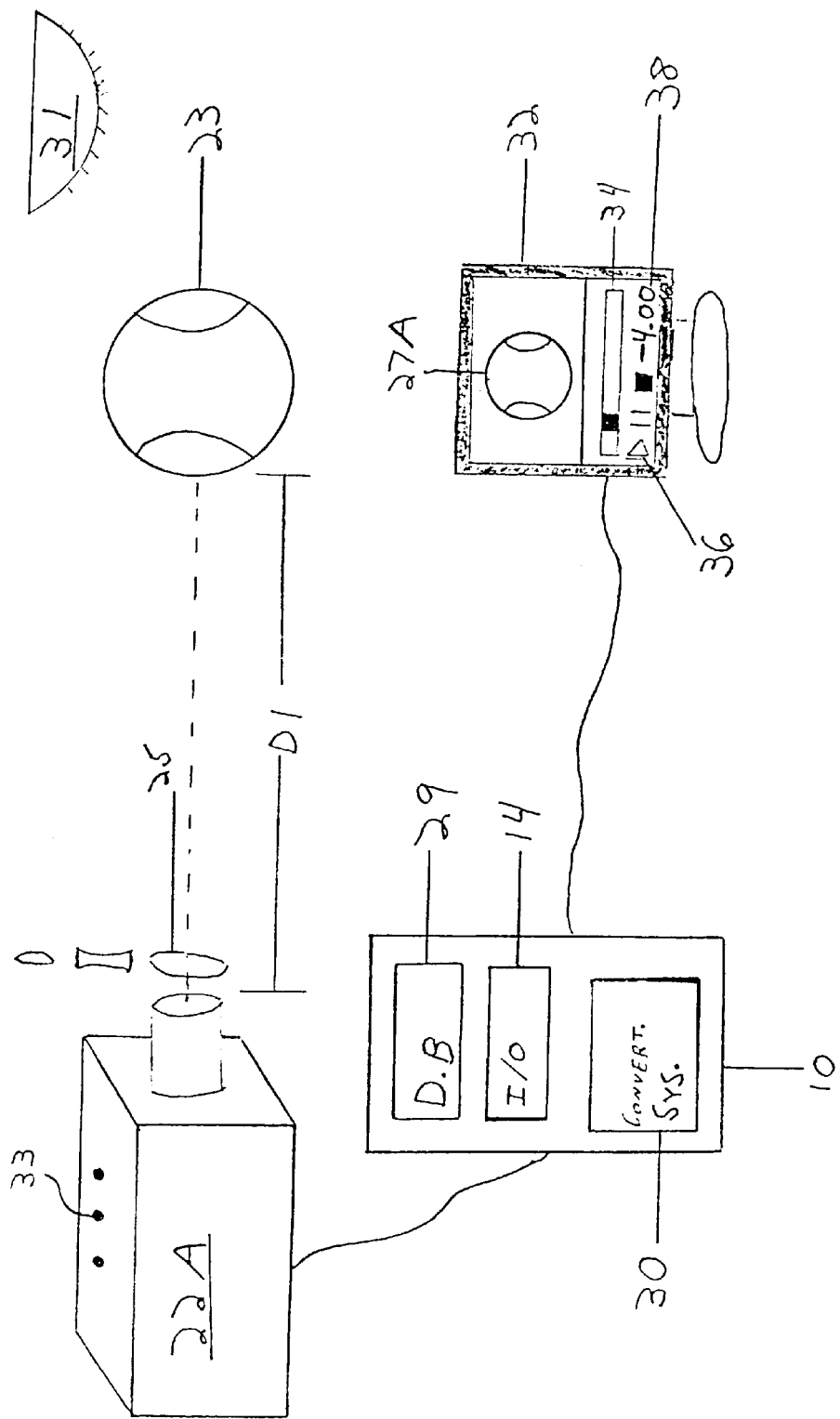
FIG. 3 depicts a diagram of a system for performing an eye examination in accordance with a first embodiment of the present invention.

Referring now to FIG. 3, a system for performing an eye examination according to the first embodiment of the present invention is shown. As depicted, recording mechanism 22A records a video of an object 23. Video is meant to refer to any type of continuous video recordation, such as a video MPEG or AVI file, or a streaming video. Preferably, the recording mechanism 22A of this embodiment is a digital video recorder, however, it should be understood that other video recorders will suffice. Having access to the video of the object 23 is computer system 10. Such access can be achieved by linking the recording mechanism 22A to the computer system 10 via any hard wire or remote connection. It should be appreciated, however, that when using a digital video recorder the video of the object may be recorded to a recordable medium such as a diskette or cd-rom. In this case, no direct connection is necessary since the recordable medium can be directly transferred to the computer system 10, as known to those of ordinary skill in the art. In addition, the object 23 is shown throughout the figures as a ball, but it should be understood that any object may suffice for all embodiments of the present invention. For example, object 23 can be any letter(s), word(s), number(s), color(s), shape(s), or any combination thereof deemed most suitable by the system operator for the particular disorder being diagnosed, such as a Snellen chart.

As the object 23 is being recorded by the recording mechanism 22A, the appearance thereof is altered over time by the system operator. This can be accomplished by utilizing a variety of appearance altering means. For example, appearance altering media 25 can be inserted between the object 23 and the recording mechanism 22A as the object is being recorded. Appearance altering media 25 preferably comprises optical lenses and/or filters, depending on the refractive error being tested. The appearance altering takes place by inserting the media 25 between the recording mechanism 22A and the object and, if desired, by changing the media 25 throughout the recording. An alternative way to alter the appearance of the object 23 over time is to adjust the recording mechanism 22A. Specifically, adjustment of the zoom and focus controls 33 of the recording mechanism 22A will have a similar effect on the appearance of the object 23 as the use of altering media 25. It should be appreciated, that the various appearance altering means cited herein are not intended to be exhaustive and other known systems may be utilized. For example, the appearance of the object 23 can be altered by using a combination of media 25 and adjustments to the recording mechanism 22A, by adjusting the distance D1 of the object 23 from the recording mechanism 22A, or by adjusting a light source 31 adjacent the object 23.

Once recorded, the video can be stored in the database 29 or fed directly through to the user for real-time examination. Users accessing the system 10 can view the appearance 27A of the object on a display 32. The user has the capability to control the video through the manipulation system 36. For example, as the video is being played, the user can pause, stop, reverse or advance the video using a slide bar.

The invention further includes a converting system 30, which is executable by the computer system 10. Preferably, converting system 30 is a program stored on the memory of the computer system 10. The converting system 30 accesses the video and determines a prescription 38 corresponding to each appearance 27A of the object 23 as it appears on the video. This may be accomplished by correlating the changes in appearance altering means (e.g., lenses, filters, focus, zoom and distance) with corresponding prescriptions. For example, the converting system 30 will be able to compute the prescription based on a particular optical lens, focus setting of the recording mechanism 22A, etc. Thus, if a first video segment is taken of the object 23 with a first lens is placed in front of the recording mechanism for 2 seconds, and a second video segment is taken with a second lens for the next 2 seconds, the converting system 30 will determine and output two prescriptions 38, one for each video segment. Therefore, the prescriptions will be dependent on the type of appearance altering means utilized so that each unique video segment that utilizes a unique appearance altering means will have a unique prescription.

The converting system 30 generally functions in the same manner for all embodiments described herein. One method for implementing the converting system 30 is to provide a prescription for each particular video segment. The prescription can be calculated by manually determining a prescription that corresponds to each appearance altering means, or by developing an algorithm that can calculate the prescription based on the type of appearance altering means utilized. In the case of the latter, the converting system 30 would only require an identifier for each image altering means utilized to calculate an associated prescription. The converting system 30 can also comprise a computerized table (e.g., one table for each video segment) that correlates a prescription value to a video segment or appearance altering means. When a user selects a video, the table that corresponds to the selected video is accessed. As the video is played, the user can pause, advance or reverse the video until the best appearance of the object is determined. As the appearance is altered (by the system operator in this first embodiment), the displayed prescription 38 will alter correspondingly.

It should be understood that the system operator can be an individual or the computer system executing a pre-programmed routine showing the object at different appearances. In addition, it should be appreciated that portions of the video may be of the object 23 without appearance altering means being utilized.

Figure 4A:
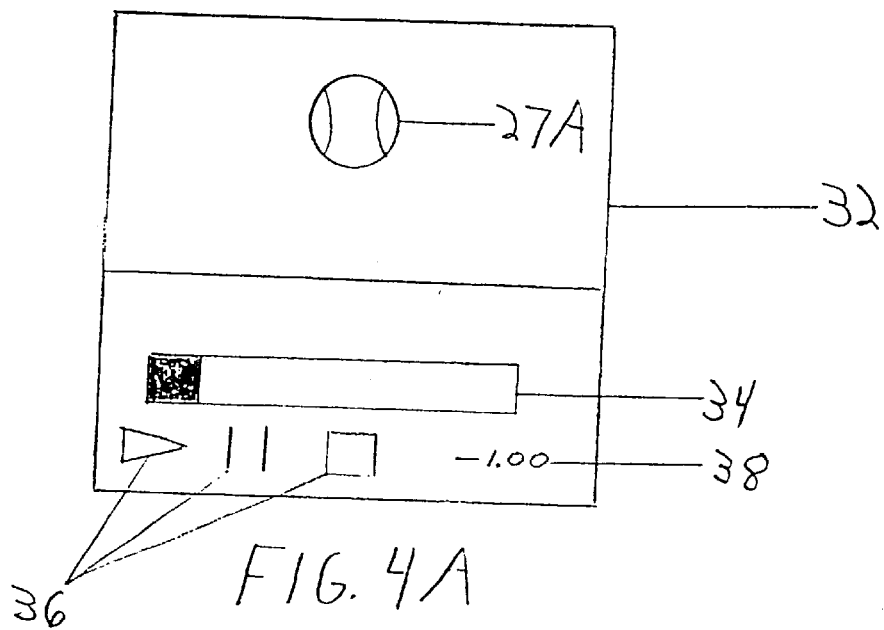
FIG. 4A depicts a display showing an appearance of an object in accordance with the first embodiment of the present invention.
Figure 4B:
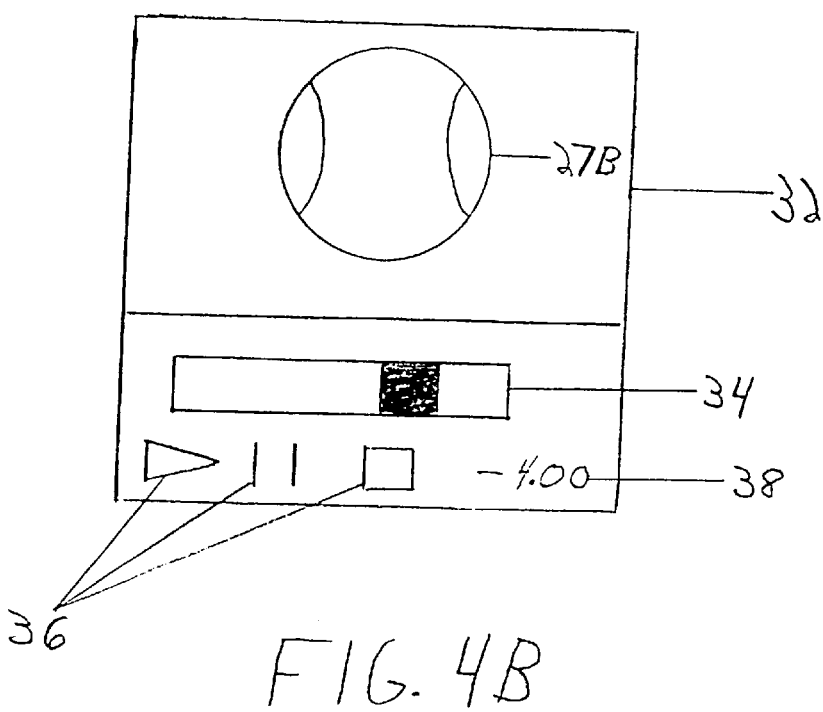
FIG. 4B depicts a display showing an appearance of an object after alteration in accordance with the first embodiment of the present invention.

Referring now to FIGS. 4A and 4B, the appearance of the object 27A and 27B at two different times/alterations is shown. As first shown in FIG. 4A, the appearance 27A of the object 23 is a first size at a first time point. The prescription 38 that corresponds to this appearance 27A is displayed on the display 32 for the user to view. FIG. 4B shows the same video of the object advanced to a second time point, as evidenced by the change in appearance 27B of the object 23 as well as the position of the video manipulation system 34. As depicted, the appearance 27B of the object 23 has changed relative to that shown in FIG. 4A and can continue to be altered over time as many times as the system operator desires. Using the manipulation system 34, the user will identify the best appearance 27A or 27B of the object 23. Once this has been determined, the user and/or the computer system can note the corresponding prescription 38 and obtain any necessary eye wear. As indicated above, the video may contain time intervals where no appearance alteration means are used. If one of these time intervals is selected by the user as having the best appearance, the converting system 30 can report that no prescription is required, or in the alternative, indicate a prescription of plano (0.00).

It should be understood that the two appearances of the object 23 are shown in FIGS. 4A and 4B are for illustration purposes only, and the precise quantity, quality and type of appearances displayed is not intended to be limiting.

Figure 5:
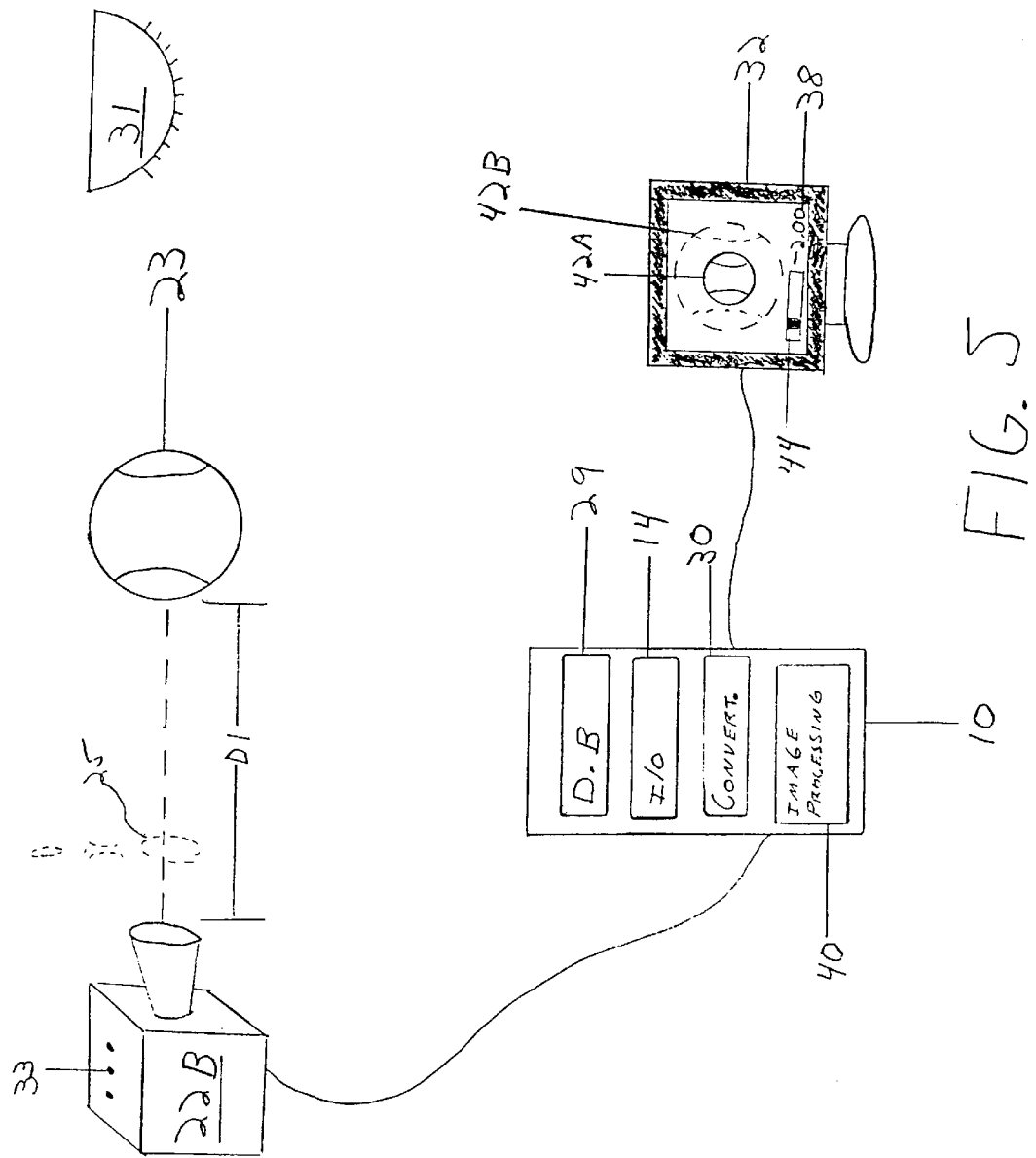
FIG. 5 depicts a diagram of a system for performing an eye examination in accordance with a second embodiment of the present invention.

Referring now to FIG. 5, a second embodiment of the present invention is shown. In this embodiment, the recording mechanism 22B will capture a still image or snapshot (as opposed to a continuous video) of the object 23. Preferably, the recording mechanism 22B is a digital camera, however, it should be understood that any camera capable of taking snapshots may suffice. Similar to the first embodiment, the image is transferred to the computer system 10 and is preferably stored in the database 29. However, it should be understood that if a real time image is desired, the database 29 could be eliminated. In addition, the transfer of the captured still image from the recording mechanism 22B to the computer system 10 can be accomplished through any known means, such as direct connection, remote connection, or by the transfer of a recordable medium containing the recorded image.

Upon starting the test, the user will view one still image of the object 23 on the display 32. The appearance 42A of the object 23 is then manually altered by the user, instead of through the imposition of appearance altering means as described for the first embodiment. The manual alteration is accomplished by the image processing system 40, which is executable by the computer system 10. This system 40 allows the user to utilize the manipulation system 44 to alter the appearance 42A of the object 23. Similar to the first embodiment, the appearance can be varied in focus, zoom, size, color, position, or in any other useful way to diagnose refractive errors. Accordingly, manipulation system 44 may include any quantity of controls. Altering images using image processing system 40 is well known in the art and such examples can be found in commonly used graphics or drawing programs as well as in Photoshop by Adobe.

As the user manually alters the appearance 42A of the object 23, the converting system 30 communicates with the image processing system 40 to determine a prescription 38 that corresponds to the particular appearance 42A of the object 23 at the present time. Thus, when the user alters the appearance of the object 23 from 42A to 42B, the prescription is altered as well. The converting system 30 for calculating a prescription will be similar to that described above for the first embodiment. For example, the prescription that corresponds to each particular appearance and alteration can be stored in a table, or calculated using an algorithm. If a table is used, converting system 30, will access the prescription 38 that corresponds to the particular appearance 42A on the display 32.

It should be appreciated that the preferred means of altering the appearance 42A of the object 23 is manually by the user. However, manual alteration can be used in combination with the various appearance altering means described in the first embodiment and imposed by an operator. For example, the manual alteration can be used in combination with appearance altering media 25, recording mechanism controls 33, light source 31, and/or distance adjustment D1. In such a case, the converting system 30 would coordinate with the image processing system 40 to determine and display the prescription. In the case where no appearance alteration (manual or otherwise) is needed for the user to identify a best appearance, the converting system 30 can either not report a prescription or report a prescription of piano.

Figure 6A:
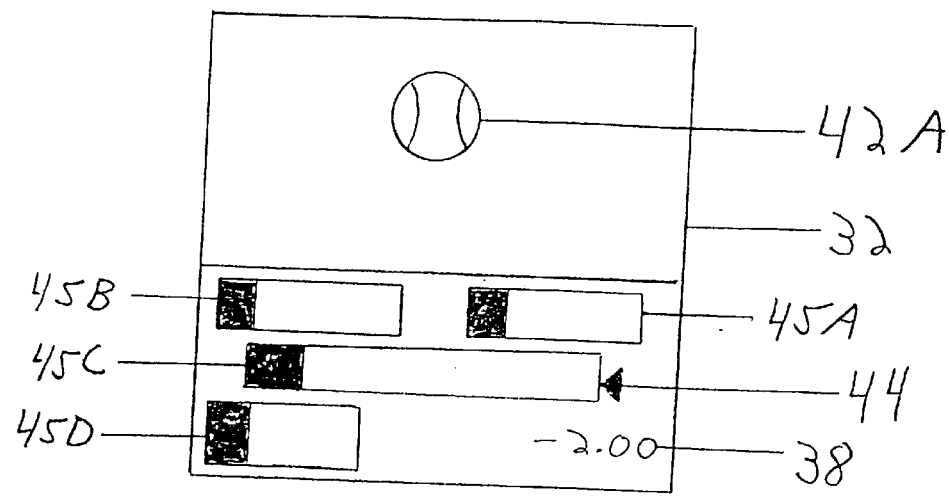
FIG. 6A depicts a display showing an appearance of an object in accordance with the second embodiment of the present invention.
Figure 6B:
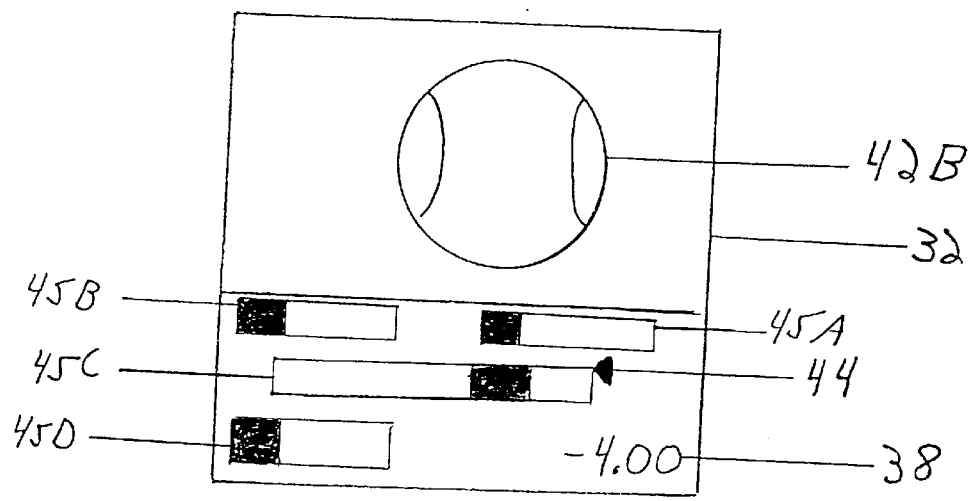
FIG. 6B depicts a display showing an appearance of an indica after alteration in accordance with the second embodiment of the present invention.

Referring to FIGS. 6A and 6B, the image of the object is shown in two different appearance states. FIG. 6A shows the appearance 42A of the object 23 prior to alteration and having a first prescription −2.00. FIG. 6B shows the appearance 42B of the object 23 after the appearance has been manually altered by the user using slide bar 44. As depicted, both the appearance 42B and prescriptions 38 have been altered. Also shown in both FIGS. 6A and 6B, the manipulation system 44 can include any number of controls. For example, the manipulation system can include focus controls 45A, zoom control 45B, size control 45C and color control 45D for the user to adjust. This will aid in ensuring that the computerized examination is simulative of an in-person examination.

It should be understood that the two appearances of the object 23 are shown in FIGS. 5, 6A and 6B are for illustration purposes only, and the precise quantity, quality and type of appearances displayed is not intended to be limiting.

Figure 7:
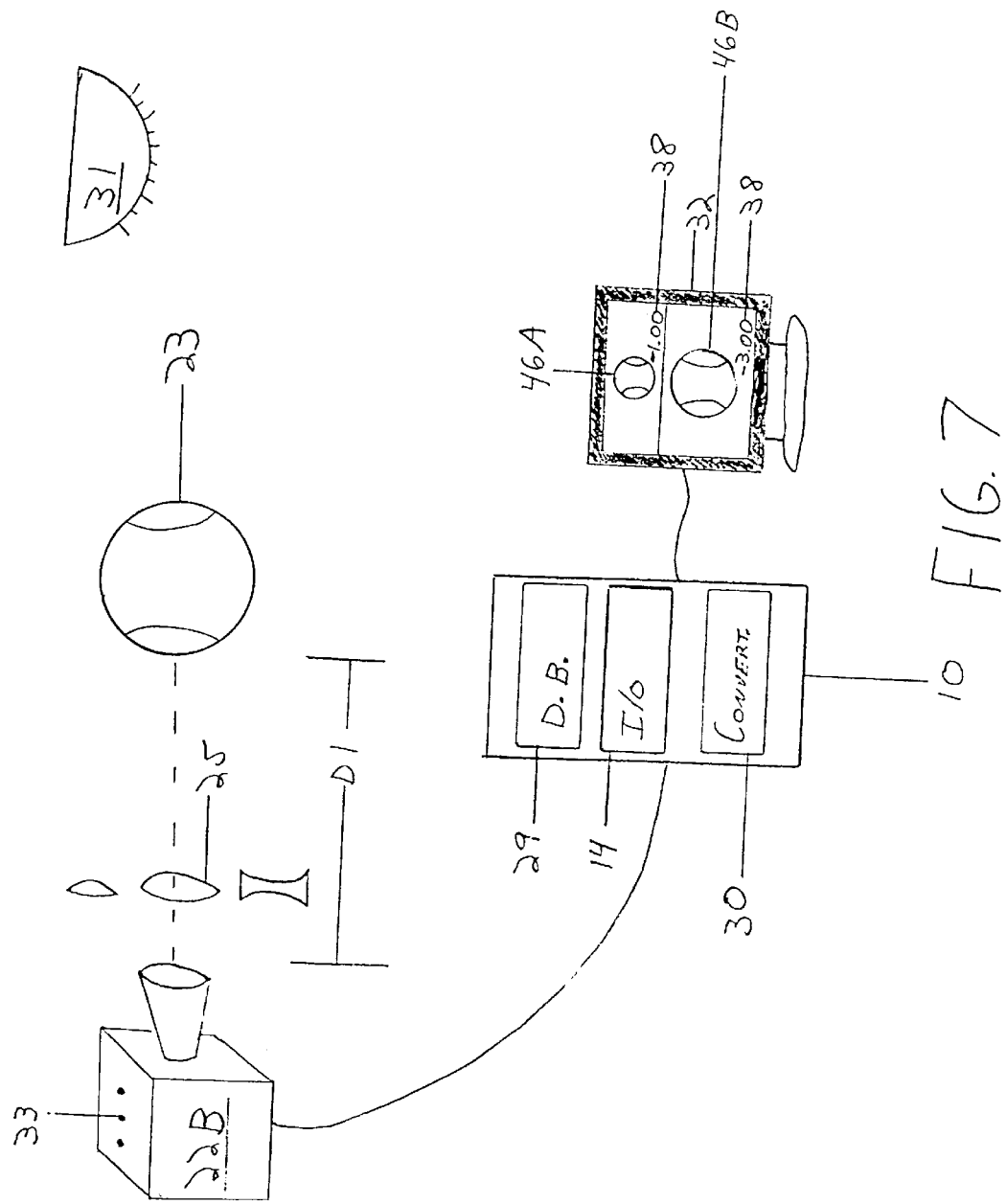
FIG. 7 depicts a system for performing an eye examination in accordance with a third embodiment of the present invention.

Referring now to FIG. 7, a third embodiment of the present invention is shown. As depicted, the recording mechanism 22B will capture a plurality of still images or snapshots of the object 23 (one per appearance altering means utilized). Preferably, the recording mechanism 22B is a digital camera, however, it should be understood that any camera capable of taking snapshots may suffice. Similar to the previous embodiments, the images are preferably transferred to the database 29 of the computer system 10 through any known means (e.g., direct connection, remote connection or transfer of recordable medium containing the captured image. It should be understood, similar to the previous embodiments, that real time examination can occur in which case, the database 29 could be eliminated.

As the plurality of images are being captured, the appearance 46A of the object 23 is altered by the various appearance altering means described above. Specifically, the operator can adjust the controls 33 of the recording mechanism 22B, impose an appearance media 25 (e.g., lens or filter) between the recording mechanism 22B and the object 23, manipulate light source 31 or alter the distance D1 between the recording mechanism 22B and the object 23. For each appearance altering means utilized, a new still image of the object 23 is captured. Therefore, the user will access the computer system 10 and look through each captured image as the appearance 46A thereof varies over time or from image to image. Similar to previously described embodiments, each appearance is grouped with its corresponding prescription based on the appearance altering means utilized. The function of determining the prescription is performed by the converting system 30 in a similar manner as described above for the first embodiment. For example, the prescription that corresponds to a particular altering means can be stored in a table in the converting system 30. Once the best appearance 46A or 46B is identified by the user, the corresponding prescription 38 is noted.

Figure 8A:
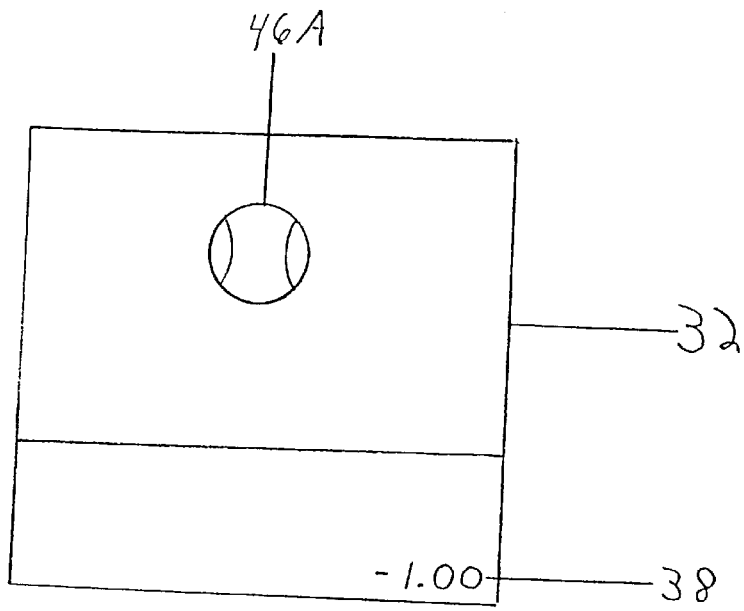
FIG. 8A depicts a display showing an appearance of an object in accordance with the third embodiment of the present invention.
Figure 8B:
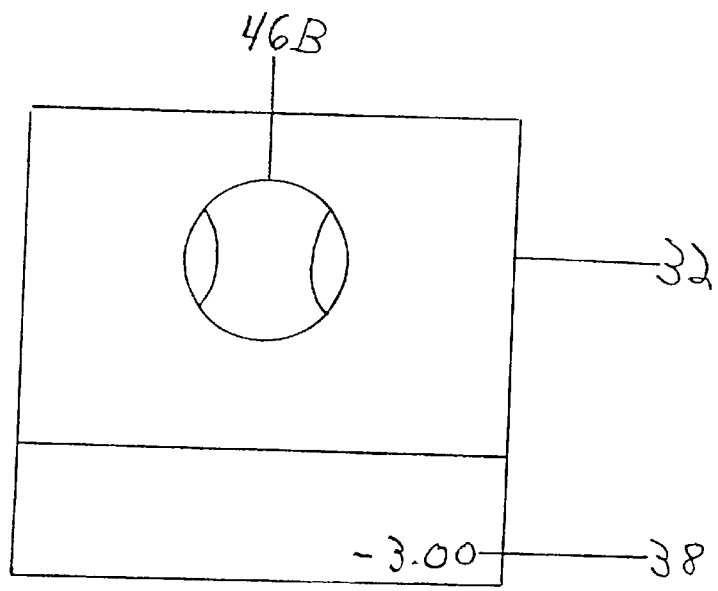
FIG. 8B depicts a display showing an appearance of an object after alteration in accordance with the third embodiment of the present invention.

Referring to FIGS. 8A and 8B, the object 23 is shown at two different appearance stages in accordance with the third embodiment. FIG. 8A represents a first appearance 46A for the object and its corresponding prescription 38. FIG. 8B shows the appearance 46B and corresponding prescription 38 as altered from FIG. 8A. It should be understood, that certain images of the object 23 may be captured without the use of image altering means. In this case, either no prescription will be reported or a prescription of plano can be reported.

It should be understood that the two appearances of the object 23 are shown in FIGS. 7, 8A and 8B are for illustration purposes only, and the precise quantity of appearances displayed is not intended to be limiting. Moreover, the display 32 depicts two appearances displayed simultaneously, however, it should be appreciated that the appearances can be displayed in more or fewer quantity at one time.

Referring now to FIG. 9, a fourth embodiment of the present invention is shown. In this embodiment, a still image of the object 23 is captured by the recording mechanism 22B, which is preferably a digital camera. However, it should be appreciated that any camera/mechanism capable of taking snapshots will suffice. The image is preferably transferred to the database 29 of the computer system 10 through any of the known means described above. However, if real time examination is desired, the database can be eliminated 29. When a user accesses the computer system 10, the image of the object will be displayed. The appearance 48A of the object 23 can be altered by the user by viewing the display 32 through at least one optical lense 50. Thus, the user is manually altering the appearance 48A of the object 23. Once the best appearance of the object is ascertained by the user, reference is made to the converting source 52. From here, the user can ascertain their prescription by cross-referencing the optical lens 50 that yielded the best appearance. Converting source 52 is preferably a computerized or hard-copy table listing the various lenses 50 with their corresponding prescription. The optical lenses 50 and converting source 52 can be obtained by the user through any known means (e.g., mailing and/or downloading, etc.) and are preferably provided by the operator.

The appearance 48A of the object 23 can also be altered by utilizing other appearance altering means in combination with the optical lenses 50. For example, the recording mechanism 22B can be adjusted, the distance D1 between the object 23 and the recording mechanism 22B can be adjusted or the light source 31 can be adjusted. For each appearance altering means utilized, a separate image should be recorded by the recording mechanism 22B and accessed by the computer system 10. The user will then view each appearance 48A and 48B through the lenses 50 to determine the best appearance. In this case, the converting source 52 should cross-reference the appearance altering media as well as the lenses 50. It should be understood that two appearances are shown in FIG. 9 for illustration purposes only and the precise quantity of appearances displayed is not intended to be limiting.

Figure 10:
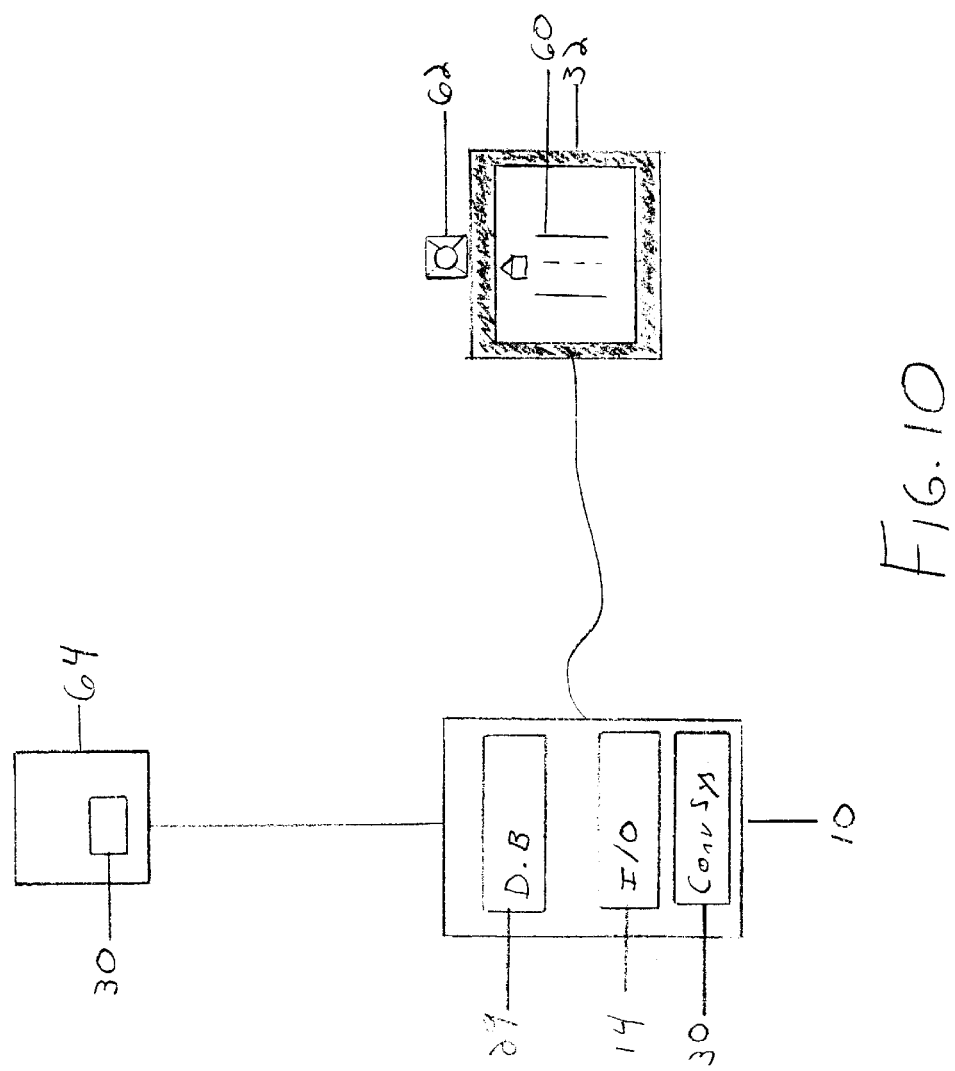
FIG. 10 depicts a system for performing an eye examination in accordance with a fifth embodiment of the present invention.

Referring now to FIG. 10, a fifth embodiment of the present invention is shown. In this embodiment, an approximate prescription of a user is taken using auto-refractor 64 and recording mechanism 62. Specifically, image 60 is transmitted from auto-refractor 64 to computer system 10, similar to all previous embodiments, such transmission can occur via any hard wire or remote connection. The transmitted image 60 will be displayed on display 32. As this occurs, recording mechanism 62 will record the response of the user's eyes to image 60. Preferably, the recording mechanism 62 of this embodiment is either a digital video recorder or a digital camera, however, it should be understood that other video recorders will suffice. Additionally, it should be understood that recording mechanism 62 and display 32 can be present in a single unit thereby providing the display of image 60 on the recording/display mechanism. Recording mechanism 62 could be situated to allow the user to look directly into recording mechanism 62 while viewing the display of image 60.

It should be appreciated that as image 60 is being transmitted from auto-refractor 64, it can be stored in database 29. This allows the test to be run at any time using the stored image. Alternatively, the image can be transmitted in real-time to display 32. Similarly, the response of the user's eyes as recorded by recording mechanism 62 can be stored in database 29 or transmitted directly back to auto-refractor 64 in real-time. In addition, it should be appreciated that when using a digital recording mechanism, the captured response of the user's eyes may be recorded to a recordable medium such as a diskette or cd-rom. In this case, no direct connection between recording mechanism 62 and computer system 10 is necessary since the recordable medium can be directly transferred to the computer system 10, as known to those of ordinary skill in the art.

After the response of the user's eyes have been recorded, the response will be transmitted back to auto-refractor 64 for conversion by converting system 30 into an approximate prescription. The concept and functionality of an auto-refractor are well known to those of ordinary skill in the art and will not be described herein. Alternatively, similar to previous embodiments, converting system 30 could exist in computer system 10. This eliminates the need to transmit the recorded response to auto-refractor 64. In either case, the present invention allows an auto-refractor to be used over a computer system 10 and a computing network.

Figure 11:
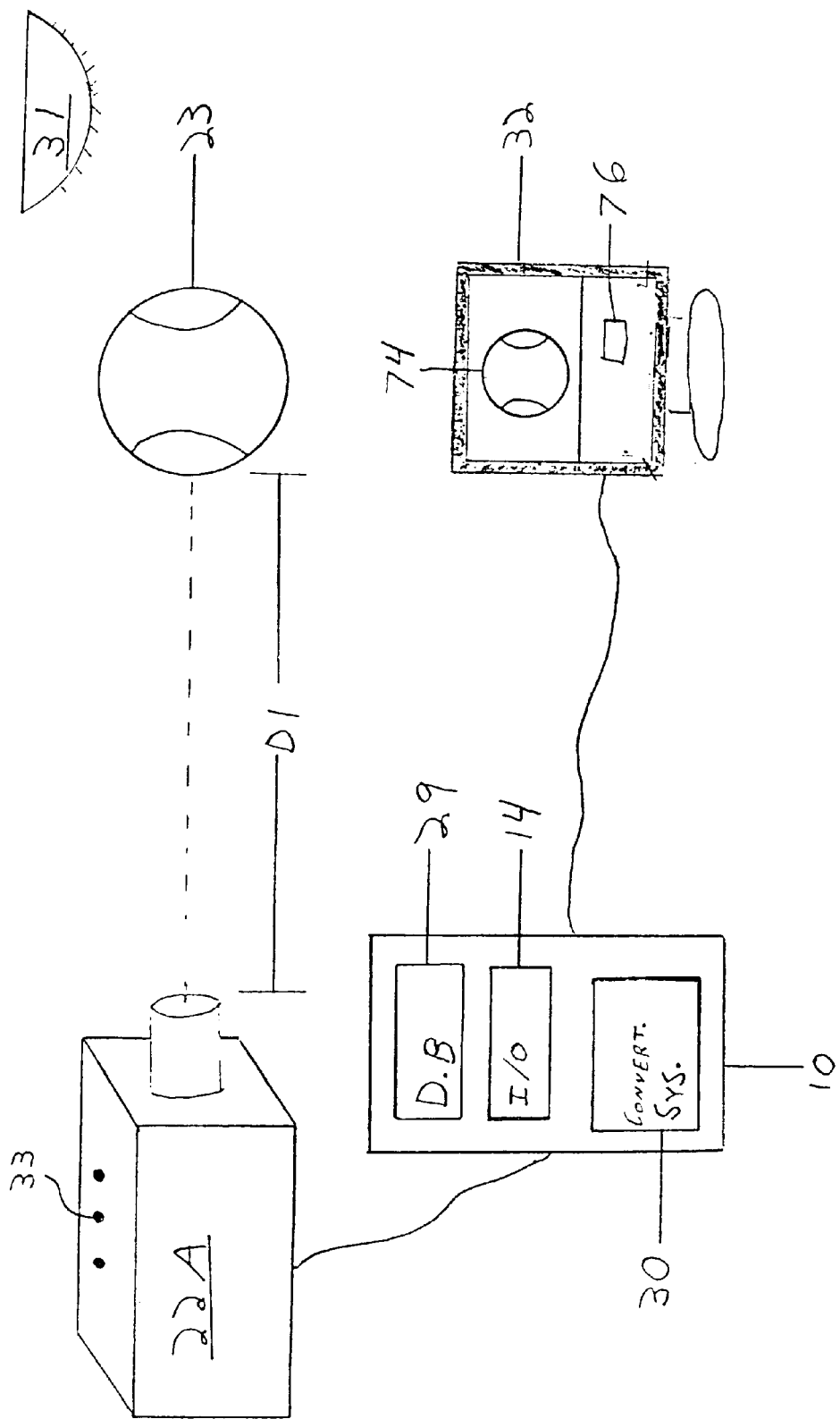
FIG. 11 depicts a system for performing an eye examination in accordance with a sixth embodiment of the present invention.

Referring now to FIG. 11, a sixth embodiment of the present invention is shown. As depicted, recording mechanism 22A records a video of an object 23. Video is meant to refer to any type of continuous video recordation, such as a video MPEG or AVI file, or a streaming video. Preferably, the recording mechanism 22A of this embodiment is a digital video recorder, however, it should be understood that other video recorders will suffice. Having access to the video of object 23 is computer system 10. Such access can be achieved by linking recording mechanism 22A to computer system 10 via any hard wire or remote connection. It should be appreciated, however, that when using a digital video recorder the video of the object may be recorded to a recordable medium such as a diskette or cd-rom. In this case, no direct connection is necessary since the recordable medium can be directly transferred to the computer system 10, as known to those of ordinary skill in the art. In addition, the object 23 is shown throughout the figures as a ball, but it should be understood that any object may suffice for all embodiments of the present invention. For example, object 23 can be any letter(s), word(s), number(s), color(s), shape (s), or any combination thereof deemed most suitable by the system operator for the particular disorder being diagnosed, such as a Snellen chart.

As the object 23 is being recorded by the recording mechanism 22A, the focus thereof is altered over time. This is preferably accomplished by: (1) manipulating (focus) controls 33 on recording mechanism 22A; (2) adjusting distance D1 between recording mechanism 22A and object 23; and/or (3) adjusting light source 31.

Once recorded, the video can be stored in the database 29 or fed directly through to the user for real-time examination. Users accessing computer system 10 can view the appearance 74 of the object on display 32. Preferably, the video of object 23 at each focus level will be displayed on display 32 for a length of time (e.g., 5 seconds). When the user sees the object in the best focus, he/she can select the corresponding focus level via selection system 76, or the like. Based upon the user's selection, converting system 30 will convert the focus level into a prescription. Converting system 30 functions as described above in conjunction with FIG. 3. Specifically, converting system 30 comprises any system (e.g., table, algorithm, etc.) for correlating a focus level with a prescription. Based upon the determined prescription, the user could order appropriate lens wear via a hyperlink or the like.

It should be understood that this embodiment could also be carried out with a camera recording mechanism capable of taking snapshots (e.g., recording mechanism 22B of FIG. 5). Preferably, a digital camera is used, but it should be understood that any camera could suffice. In either event, numerous images of object 23, at different focuses, would be recorded. As indicated above, the focus could be adjusted by: (1) manipulating focus controls on recording mechanism 22B; (2) adjusting distance D1; and/or (3) adjusting light source 31. Each image could then be displayed on display 32 for a period of time (e.g., 5 seconds), thus, allowing the user to select the best focus level. Converting system 30 would then convert the selected focus level into a prescription.

Figure 12:
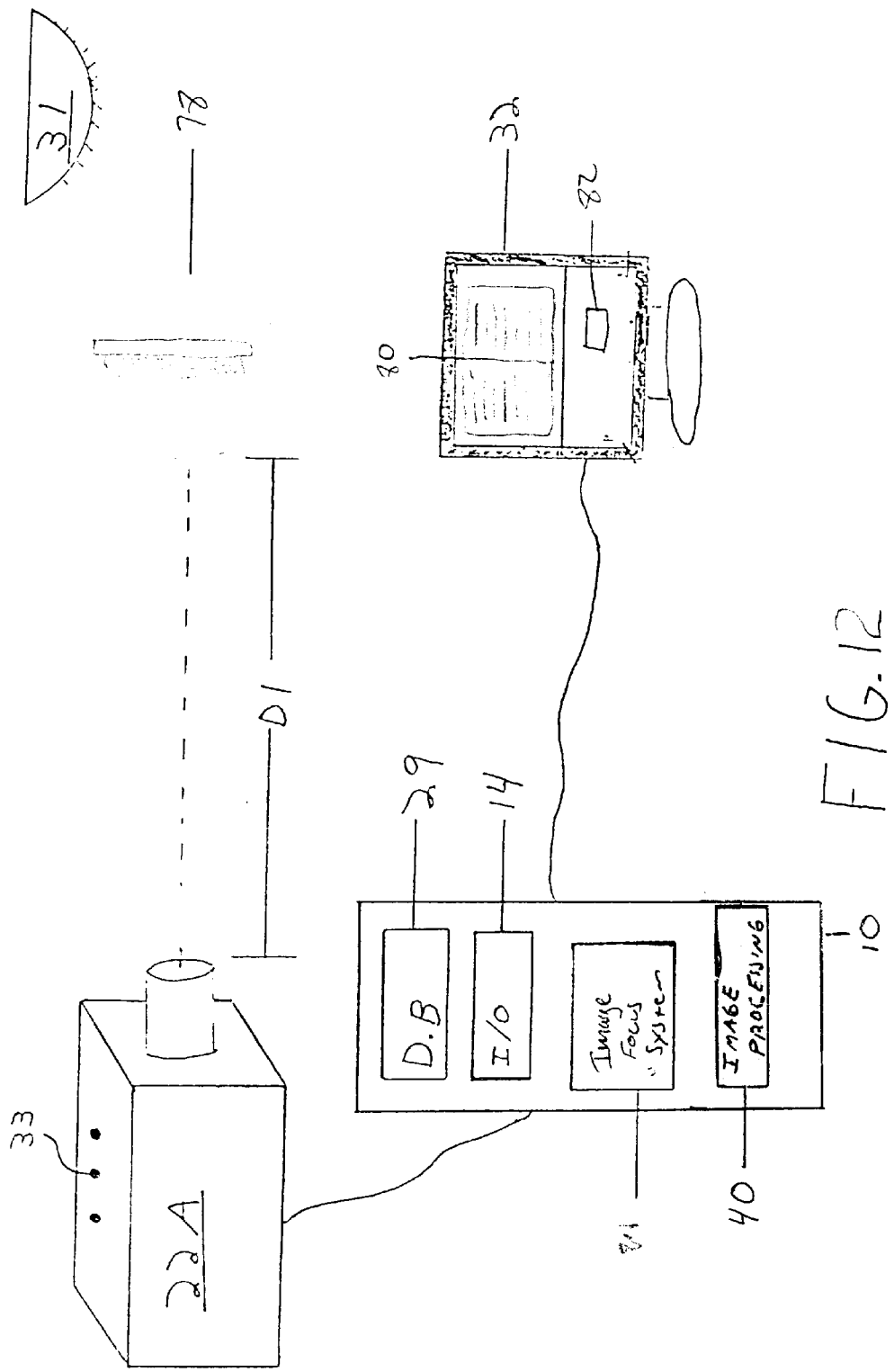
FIG. 12 depicts a system for performing an eye examination in accordance with a seventh embodiment of the present invention.

Referring now to FIG. 12, a seventh embodiment of the present invention is shown. As depicted, recording mechanism 22A records images from an object 78. Object 78 is a preferably a dynamic object such as a book or the like object in which different subsequent images can be recorded. As the object 78 is being recorded by the recording mechanism 22A, the magnification thereof is altered over time. This is preferably accomplished by: (1) manipulating controls 33 on recording mechanism 22A; (2) adjusting distance D1 between recording mechanism 22A and object 78; and/or (3) utilizing image processing system 40.

Once recorded, the video can be stored in the database 29 or fed directly to the user for real-time examination. Users accessing computer system 10 can view the appearance 80 of the object on display 32. Preferably, the video of object 78 at each magnification level will be displayed on display 32 for a length of time (e.g., 5 seconds). When the user sees the object in the best focus, he/she can select the corresponding magnification level via selection system 82. Based upon the user's selection, image focus system 84 will display subsequent images of the object (e.g., subsequent pages from the book) at the selected magnification level. This can occur by image focus system 84 communicating the selected magnification level back to the recording mechanism 22A (or an operator thereof), which will record subsequent images of the object 78 at the selected magnification level. Alternatively, this can occur by image focus system 84 communicating the selected magnification level to image processing system 40, which will show all subsequent images at the selected magnification level (as described above).

It should be understood that this embodiment could also be carried out with a camera recording mechanism capable of taking snapshots (e.g., recording mechanism 22B of FIG. 5). Preferably, a digital camera is used, but it should be understood that any camera could suffice. In either event, numerous images of object 78, at different magnifications, would be recorded. As indicated above, the magnification could be adjusted by: (1) manipulating controls on recording mechanism 22B; (2) adjusting distance D1; and/or (3) image processing system 40. Each image could then be displayed on display 32 for a period of time (e.g., 5 seconds), thus, allowing the user to select the best magnification level. Image selection system 84 would then display subsequent images at the selected magnification level (as described above).

The foregoing description of the preferred embodiments of this invention has been presented for purposes of illustration and description. It is not intended to be exhaustive or to limit the invention to the precise form disclosed, and obviously, many modifications and variations are possible. Such modifications and variations that may be apparent to a person skilled in the art are intended to be included within the scope of this invention as defined by the accompanying claims.

What is claimed is:

1. A system of performing an eye examination, comprising:
   a computer system linked to an auto-refractor over a computer network, wherein the auto-refractor and the computer system are separate components;
   a display linked to the computer system for displaying an image from the auto-refractor; and
   an image recording mechanism for independently recording a response of a user's eye to the displayed image, wherein a prescription is determined from the recorded response.

2. The system of claim 1, wherein the prescription is determined by the auto-refractor.

3. The system of claim 1, wherein the recording mechanism is positioned proximate the display.

4. The system of claim 1, further comprising a database for storing the image and the recorded response.

5. The system of claim 1, wherein a single assembly comprises the recording mechanism and the display.

6. A system for performing an eye examination, comprising:
   an image generated by an auto-refractor;
   a computer system linked to the auto-refractor over a computer network for receiving the generated image, wherein the system and the auto-refractor are separate components;
   a display linked to the computer system for displaying the received image; and
   a recording mechanism for independently recording a response of a user's eye to the displayed image, wherein a prescription is determined from the recorded response by the auto-refractor.

* * * * *

UNITED STATES PATENT AND TRADEMARK OFFICE
CERTIFICATE OF CORRECTION

PATENT NO. : 6,761,453 B2  
DATED : July 13, 2004  
INVENTOR(S) : Wilson

It is certified that error appears in the above-identified patent and that said Letters Patent is hereby corrected as shown below:

<u>Column 14,</u>  
Line 9, after "the", first occurrence, please insert -- computer --.

Signed and Sealed this

Nineteenth Day of October, 2004

JON W. DUDAS  
*Director of the United States Patent and Trademark Office*